(12) United States Patent
Sakai

(10) Patent No.: US 8,548,121 B2
(45) Date of Patent: Oct. 1, 2013

(54) X-RAY ANALYZER

(75) Inventor: Noriaki Sakai, Chiba (JP)

(73) Assignee: SII Nano Technology Inc., Chiba (JP)

( * ) Notice: Subject to any disclaimer, the term of this patent is extended or adjusted under 35 U.S.C. 154(b) by 70 days.

(21) Appl. No.: 13/403,277

(22) Filed: Feb. 23, 2012

(65) Prior Publication Data

US 2012/0230468 A1 Sep. 13, 2012

(30) Foreign Application Priority Data

Mar. 9, 2011 (JP) ................................. 2011-052140

(51) Int. Cl.
*G01N 23/223* (2006.01)
(52) U.S. Cl.
USPC .............................................. 378/44; 378/86
(58) Field of Classification Search
USPC .......................................... 378/44–49, 86–90
See application file for complete search history.

(56) References Cited

U.S. PATENT DOCUMENTS

2010/0074405 A1* 3/2010 Saito et al. ...................... 378/44
2011/0206186 A1* 8/2011 Matsumura et al. ............ 378/87

FOREIGN PATENT DOCUMENTS

| JP | 04-175647 | 6/1992 |
| JP | 11-264805 | 9/1999 |
| JP | 2006-119108 | 5/2006 |
| JP | 2007-163183 | 6/2007 |
| JP | 2009-300232 | 12/2009 |

* cited by examiner

*Primary Examiner* — Hoon Song
(74) *Attorney, Agent, or Firm* — Brinks Hofer Gilson & Lione

(57) ABSTRACT

Provided is an X-ray analyzer that is capable of reducing measurement time necessary for mapping analysis by measuring only regions on a sample targeted by a measurer with minimal action. A superimposition process of a mapping image and image data of the sample is performed, and a position corresponding to an irradiation point is determined. Based on the result, the image is displayed, and measurement execution regions are designated on the displayed image and hence a sample moving mechanism moves at high speed in regions excluding the designated regions.

7 Claims, 4 Drawing Sheets

X-RAY ANALYZER

RELATED APPLICATIONS

This application claims priority under 35 U.S.C. §119 to Japanese Patent Application No. 2011-052140 filed on Mar. 9, 2011, the entire content of which is hereby incorporated by reference.

BACKGROUND OF THE INVENTION

1. Field of the Invention

The present invention relates to an X-ray analyzer and a mapping analysis method which are suitable for performing X-ray mapping analysis through, for example, fluorescent X-ray analysis.

2. Description of the Related Art

In fluorescent X-ray analysis, an X-ray emitted from an X-ray source irradiates a sample, and a fluorescent X-ray generated from the sample is detected by an X-ray detector. Then, a signal processing portion counts X-ray signals. From the obtained spectrum, qualitative analysis or quantitative analysis of the sample is performed.

The fluorescent X-ray analysis enables non-destructive and quick analysis, and in recent years, sensitivity of the X-ray analysis has been increased, which enables trace element measurement. Accordingly, the fluorescent X-ray analysis is used as means for detecting a harmful substance contained in a material, a composite electronic component, or the like (see, for example, Japanese Patent Application Laid-open Nos. 2006-119108 and 2007-163183).

In addition, as to X-ray mapping, there is known an X-ray mapping apparatus for analyzing a two-dimensional element distribution of a sample while scanning a sample stage, which includes an X-ray tube for irradiating the sample with an X-ray, an X-ray detector that detects a fluorescent X-ray generated from the sample, a pulse processor that discriminates X-ray energy and its intensity based on an output of the X-ray detector, a computer that processes a signal from the pulse processor, image pickup means for taking an optically observed image corresponding to a position where the X-ray intensity is obtained, a stage controller for driving the X-ray sample stage, and an image processing apparatus that displays an X-ray intensity distribution in a two-dimensional manner (for example, see Japanese Patent Application Laid-open Nos. Hei 04-175647, Hei 11-264805, and 2009-300232).

In addition, there is disclosed an X-ray mapping apparatus including a sensor for determining presence or absence of the sample at a measurement position in the above-mentioned structure of the apparatus (see Japanese Patent Application Laid-open No. Hei 11-264805).

X-ray mapping analysis is used for detecting a harmful substance contained in a composite electronic component, but it takes a remarkably long measurement time for analysis in a wide range. In Japanese Patent Application Laid-open No. Hei 11-264805, the presence or absence of the sample at the measurement position is detected so that the measurement time can be shortened. However, in analysis of a substrate on which many electronic components are mounted, there is a case where it cannot be determined whether or not the measurement is necessary based on only the presence or absence of the sample. For instance, there are problems that the measurement is performed even if there is a component for which the measurement is not needed on the substrate, and that the measurement cannot be performed because a region where a low profile component exists is erroneously determined to be a region without a sample. Therefore, sufficient reduction of the measurement time cannot be achieved.

SUMMARY OF THE INVENTION

The present invention has been made in view of the above-mentioned problems, and it is an object thereof to provide an X-ray analyzer and an X-ray mapping analysis method which are capable of reducing measurement time necessary for mapping analysis by measuring only regions on the sample targeted by a measurer with minimal action.

In order to solve the above-mentioned problems, an X-ray analyzer according to the present invention includes: a sample stage on which a sample is placed; a moving mechanism that is capable of moving the sample stage; a radial ray source that irradiates an arbitrary irradiation point on the sample with a primary radial ray; an X-ray detecting portion that detects a characteristic X-ray and a scattered X-ray radiated from the sample and outputs a signal including energy information of the characteristic X-ray and the scattered X-ray; an analyzing portion that is connected to the X-ray detecting portion and analyzes the signal; an image obtaining portion that obtains image data of the sample; an analysis processing portion that is connected to the analyzing portion and discriminates X-ray intensity corresponding to a specific element; an X-ray mapping processing portion that determines intensity contrast of at least one of color and brightness corresponding to the X-ray intensity based on a result of the discrimination by the analysis processing portion and performs X-ray mapping so as to perform a superimposition process of a resultant mapping image and the image data, thereby determining a position corresponding to the irradiation point; a display portion that displays an image based on a result of the X-ray mapping; and region designating means for designating a measurement execution region on the displayed image so as to obtain measurement region information, in which the moving mechanism for the sample moves at a higher speed in a region excluding the designated measurement execution region than a speed in the designated measurement execution region.

In addition, in the X-ray analyzer according to the present invention, the image obtaining portion can obtain and store in advance an optically observed image taken by an optical microscope or an electron microscope observation image taken by an electron microscope as sample image data.

In addition, the X-ray analyzer according to the present invention sets up a measurement order so that a time period for measuring all the designated measurement regions in the mapping region becomes shortest.

In addition, the X-ray analyzer according to the present invention includes means for storing information about measurement region information, and the information can be reused for another sample.

In addition, the present invention uses the optically observed image obtained when the mapping region information is stored, for an optically observed image of another sample obtained when the information is reused, to perform rotational correction, positional correction, and scaling correction, and hence the measurement regions can be recognized with accuracy.

According to the present invention, the following effect can be obtained.

Specifically, according to the X-ray analyzer and the mapping analysis method of the present invention, regions for which measurement is not necessary in the mapping region are designated in advance and the other regions are excluded from measurement, and hence a time period taken for unnecessary measurement can be reduced without fail, and the measurement can be performed efficiently in minimal measurement time. Usually, in detection of elements of low contents, results of mapping measurement of a plurality of frames are added, and the signal is amplified for analysis. Therefore, several times of scanning are necessary physically and hence the corresponding time is additionally necessary. In this case, if the present invention is used, measurement time and scanning time in the regions where the measurement is not necessary can be efficiently reduced and hence a large effect can be obtained in particular.

DETAILED DESCRIPTION OF THE PREFERRED EMBODIMENT

Hereinafter, an embodiment of an X-ray analyzer according to the present invention is described with reference to FIGS. 1 to 3. Note that, scales are appropriately changed in the figures herein so that each member is recognizable.

Figure 2:
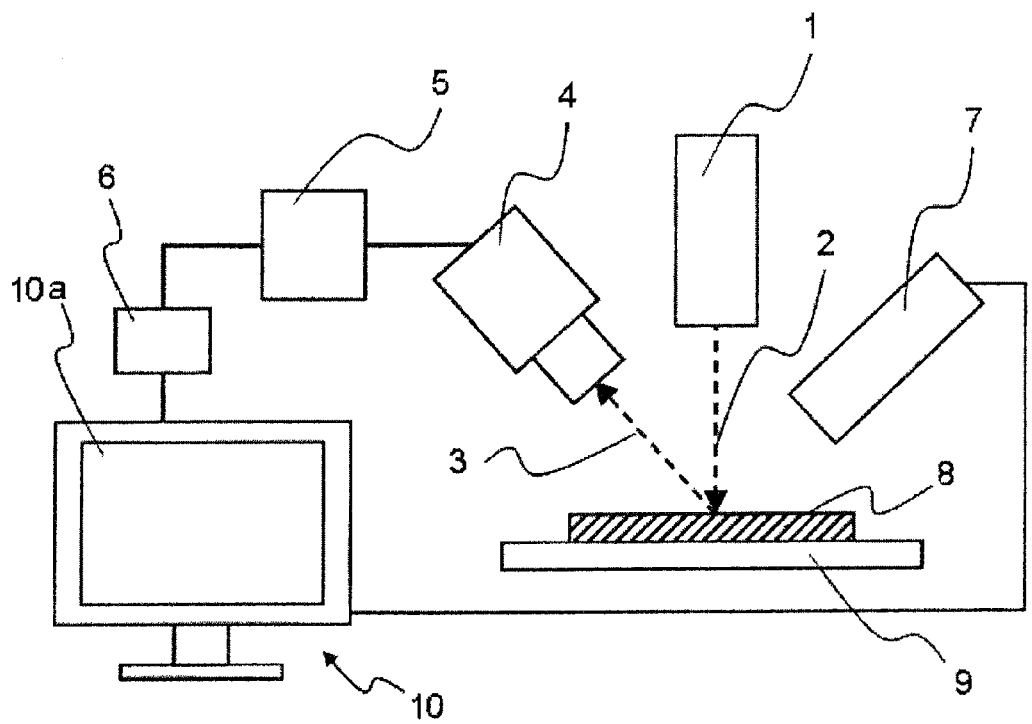
FIG. 2 is a schematic general configuration diagram of an X-ray analyzer according to the present invention.
Figure 3A:
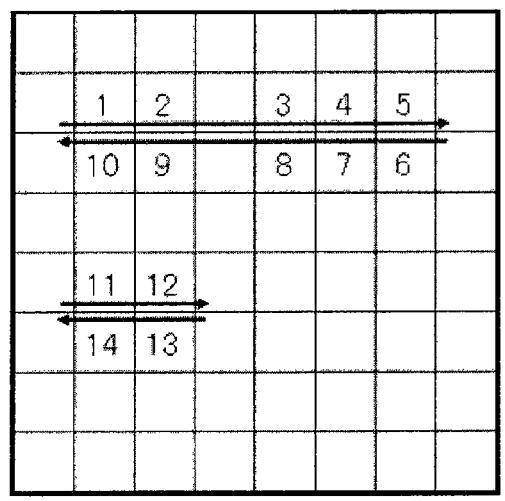
FIG. 3A illustrates a first measurement path of the measurement region according to the present invention.
Figure 3B:
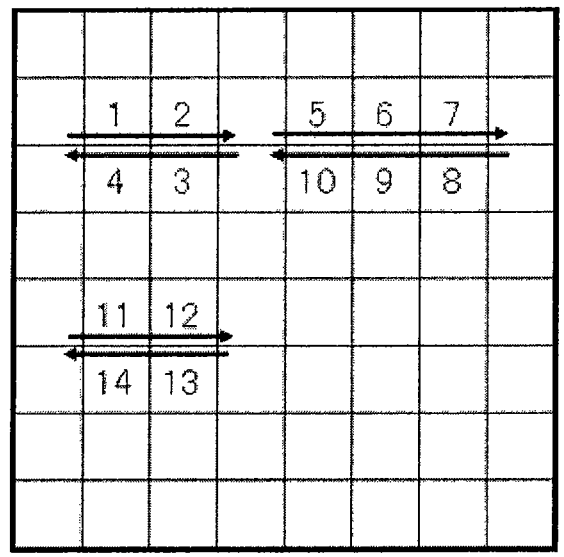
FIG. 3B illustrates a second measurement path of the measurement region according to the present invention.

The X-ray analyzer of this embodiment is an energy dispersive fluorescent X-ray analyzer, for example, which includes, as illustrated in FIG. 2, a sample stage (moving mechanism) 9 that mounts a sample 8 and is movable, an X-ray tube 1 as a radial ray source that irradiates an arbitrary irradiation point on the sample 8 with a primary X-ray (radial ray) 2, an X-ray detector 4 that detects a characteristic X-ray and a scattered X-ray 3 radiated from the sample 8 and outputs a signal including energy information of the characteristic X-ray and the scattered X-ray, an optical microscope 7 that obtains as image data an illuminated image of the sample 8 illuminated by illumination means (not shown), an analyzer 5 that is connected to the X-ray detector 4 and serves as an analyzing portion of the signal, an analysis processing portion 6 that is connected to the analyzer 5 and discriminates X-ray intensity corresponding to a specific element, an X-ray mapping processing portion 10 that determines intensity contrast of color and/or brightness corresponding to the X-ray intensity based on the result of the discrimination and performs X-ray mapping for a superimposition process of the mapping image and the image data so as to determine the position corresponding to the irradiation point, and a display 10a as a display portion for image display based on a result of the X-ray mapping.

The analysis processing portion 6 is a computer configured by a CPU and the like and functions as an analysis processing device, and discriminates the X-ray intensity corresponding to the specific element from an energy spectrum transmitted from the analyzer 5.

The X-ray mapping processing portion 10 has a function of performing the X-ray mapping based on a result of the X-ray intensity discrimination, and storing the resultant images or performing calculation or the like based on the image data. The X-ray mapping processing portion 10 sends two-dimensional image data to the display 10a. As to this function, too, a computer can be used. In addition, the X-ray mapping processing portion 10 is connected to the above-mentioned structures and has a function of controlling the structures. The X-ray mapping processing portion 10 also includes output means for displaying various types of information on the display 10a in accordance with the control.

Note that, the analysis processing portion 6 and the X-ray mapping processing portion 10 are constituted individually in FIG. 2, but may be constituted integrally by using a common computer or the like.

Further, the X-ray mapping processing portion 10 can be set to display an X-ray intensity image and an optical microscope image of the sample 8 obtained by the optical microscope 7 in a superimposed manner. In this way, the regions to be measured can be clearly recognized.

Further, the sample stage 9 is an XYZ stage which is capable of moving horizontally and vertically and being adjusted in height by means of a stepping motor (not shown) or the like in a state in which the sample 8 is fixed. The sample stage 9 is controlled by the X-ray mapping processing portion 10 so that the irradiation point is shifted relative to the sample 8 within a preset mapping region.

Next, with reference to FIGS. 1 and 2, a method of obtaining a mapping image using the X-ray analyzer according to this embodiment is described. Note that, as the sample 8, an electronic circuit board on which various electronic components such as a resistor are mounted via a solder material is used, and a concentration distribution of lead (Pb) contained in the solder material or the like is checked through the X-ray mapping. In this embodiment, measurement is performed for lead (Pb) but it is possible to perform measurement of another element or mapping measurement of a plurality of elements.

First, as illustrated in FIG. 2, the sample 8 is set on the sample stage 9 and the mapping region to be subjected to the X-ray mapping is input to the X-ray mapping processing portion 10 to be set.

Next, the sample stage 9 is driven to move the sample 8 directly below the optical microscope 7, and the mapping region of the sample 8 is imaged by the optical microscope 7. An optical microscope image thereof is transmitted to the X-ray mapping processing portion 10 to be stored. Note that, the mapping region is set in advance and then imaged by the optical microscope 7 through the above-mentioned procedure. However, the vicinity of an analysis target region of the sample 8 may be imaged by the optical microscope 7, and the mapping region may be set based on an optical microscope image thereof.

Figure 1A:
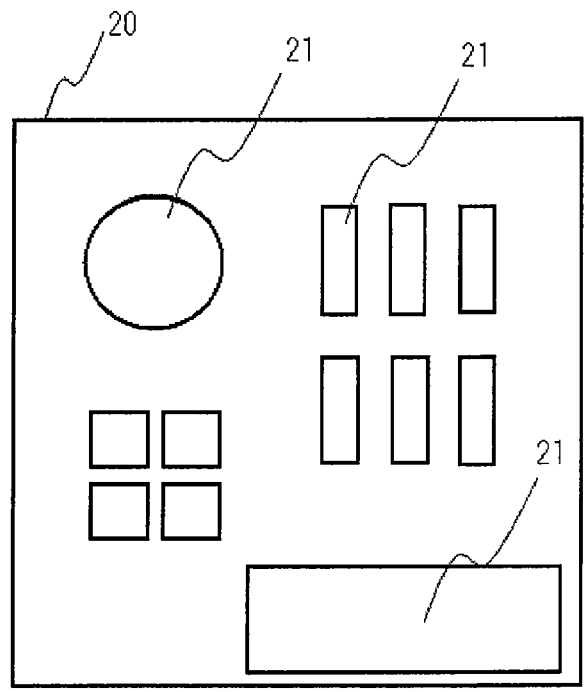
FIG. 1A is a schematic diagram of an entire mapping region of a sample according to the present invention.
Figure 1B:
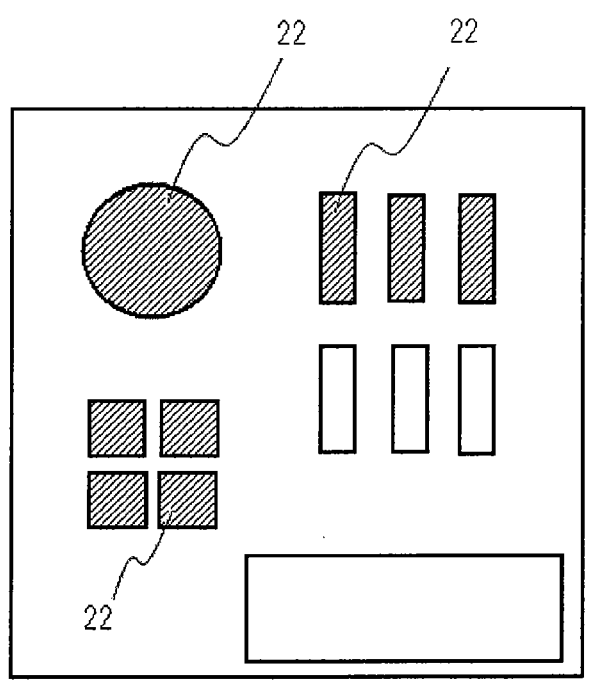
FIG. 1B is a schematic diagram of a to-be-measured component region of the sample according to the present invention.
Figure 1C:
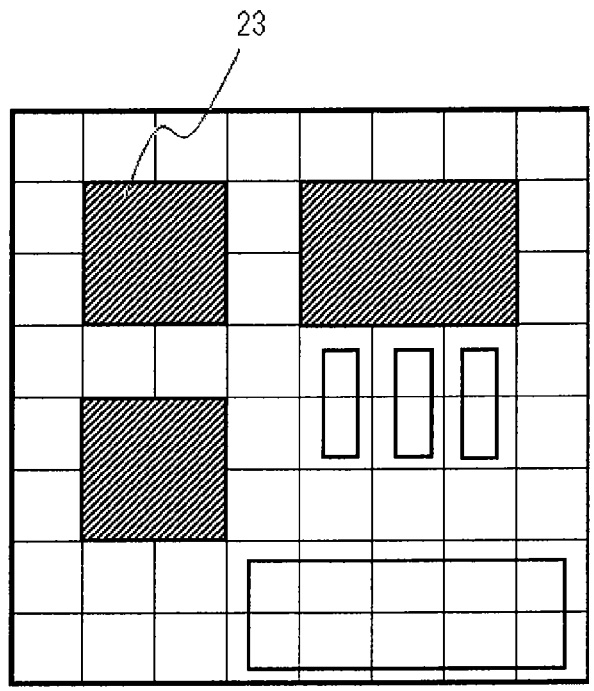
FIG. 1C is a schematic diagram at the time when a measurement region is designated in the sample according to the present invention.
Figure 1D:
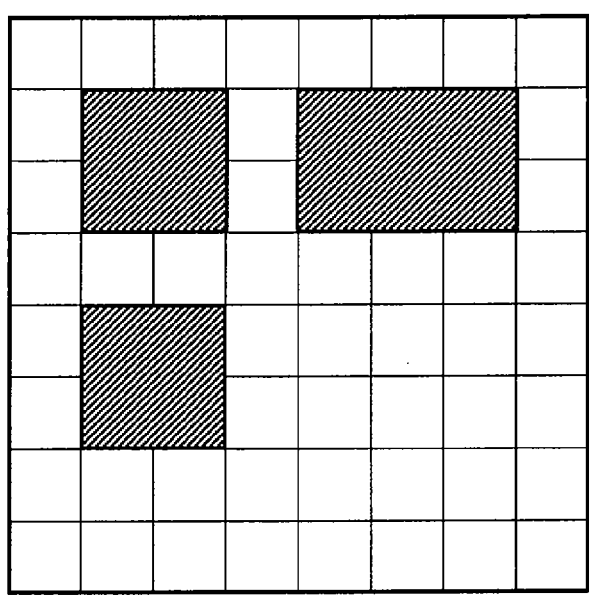
FIG. 1D is a schematic diagram of measurement region data of the sample according to the present invention.

Next, the measurement execution regions are designated. Among an entire mapping region 20 imaged by the optical microscope as illustrated in FIG. 1A, to-be-measured component regions 22 illustrated in FIG. 1B or non-measured regions as reverse regions of the to-be-measured component regions 22 are input by input means. Designation of the non-measured regions is effective, for example, in a case where an electronic component on the sample is a component that is known not to contain harmful substances in advance by an inspection method other than the mapping analysis or a component that is known to contain harmful substances inevitably for its characteristic. In this way, measurement region data illustrated in FIG. 1D is generated and is stored in the X-ray mapping processing portion 10 illustrated in FIG. 2. With this method, X-ray analysis needs to be performed only in the regions to be measured actually, and the X-ray analysis is not performed at all in the other regions. Therefore, measurement time in the non-measured region can be eliminated and hence the total time for the entire measurement can be reduced. Further, a stage travel speed in the non-measured region is set higher than a speed in the measurement region and hence the measurement can be performed at higher speed.

Next, the X-ray mapping processing portion 10 calculates and determines a measurement order based on the input measurement region data so that the time necessary to complete the measurement of all the measurement regions becomes shortest. For instance, when the measurement region data of FIG. 1D is used, it is conceivable to adopt a first measurement path illustrated in FIG. 3A. However, considering a relationship among speed adjustment time related to driving of the sample stage 9, a mapping measurement speed, an idle travel distance in which the measurement is not performed, and the like, it is possible to adopt a second measurement path illustrated in FIG. 3B. Therefore, in this determination, a simulation about which path makes measurement time shorter is performed, and the path for the shortest time is selected.

Next, in order to perform fluorescent X-ray analysis, the X-ray mapping processing portion 10 drives the sample stage 9 to move the sample 8, and places an initial irradiation point within the mapping region at an irradiation point of the primary X-ray 2 emitted from the X-ray tube 1. The sample 8 is irradiated with the primary X-ray 2 from the X-ray tube 1 in this state, and the characteristic X-ray and the scattered X-ray 3 thus generated are detected by the X-ray detector 4.

The X-ray detector 4 detects the X-ray and then transmits a signal thereof to the analyzer 5, and the analyzer 5 extracts an energy spectrum from the signal and outputs the extracted spectrum to the analysis processing portion 6 to discriminate an X-ray intensity corresponding to lead as a specific element. The discrimination result is output to the X-ray mapping processing portion 10. The X-ray mapping processing portion 10 stores, based on X-ray data of the lead, the X-ray intensity as a mapping image measurement result together with coordinate information on the irradiation point.

Further, the irradiation point is sequentially moved based on the measurement region data, and is scanned in matrix, that is, scanned two-dimensionally. Then, the detection described above is repeated for a plurality of irradiation points over the designated measurement regions in the entire mapping region, and the mapping measurement results of the respective irradiation points are stored.

The regions in which the mapping measurement is not performed in the entire mapping region are regarded as regions for which no X-ray signal is obtained, and the regions are excluded from the calculation of color or brightness. Thus, it is possible to display the mapping image with correct contrast.

Next, a method of inputting the measurement region data illustrated in FIG. 1D, namely the regions where the mapping measurement is performed, or reverse regions where the mapping measurement is not performed is described with reference to FIGS. 1A to 1D.

With reference to the optical microscope image of FIG. 1A obtained by imaging the sample 8, positions of the components 22 for which the mapping measurement is necessary are input. For the input, input means such as a mouse of a computer is used, and a region enclosed by a rectangle or an ellipse is drawn and designated in a superimposed manner on the optical microscope image as illustrated in FIG. 1C. The result is the measurement region data illustrated in FIG. 1D. This measurement region data can be stored as a bitmap image file, for example, which can be reused for mapping measurement of the same type of substrate. In the example of FIGS. 1A to 1D, the measurement action is not performed in hollow cells in the measurement region data of FIG. 1D in the entire mapping region. Therefore, the measurement time can be greatly reduced. Further, a stage travel speed in the non-measured region is set higher than a speed in the measurement region and hence the measurement can be performed at higher speed.

In addition, FIGS. 1A to 1D illustrate the example in which the entire mapping measurement region is divided into 8×8 cells for measurement as illustrated in FIGS. 1C and 1D, and the actual measurement is performed for each cell. This number of division can be set arbitrarily based on shapes of components or the like, and hence rough or dense data can be selected in accordance with measurement circumstances.

The measurement region data can be read externally when the next or subsequent mapping measurement is performed, and is displayed in a superimposed manner on the optical microscope image obtained by imaging the sample 8. In this case, there may occur misregistration depending on a method of setting the sample, a shape deviation, or the like. In this case, it is possible to designate a precise measurement position by performing positional correction, rotational correction, or scaling correction of the measurement region. The correction is performed by designating a plurality of points to be references of the measurement. In addition, the correction may be performed automatically using image processing such as pattern matching or the like.

In addition, it is possible to use drawing data of CAD or the like of the measurement sample for inputting the measurement regions. Position information of components located on the substrate is read from the input drawing data of CAD or the like, and the X-ray mapping processing portion 10 can recognize the measurement regions to perform the mapping measurement. In this case, it is also possible to correct misregistration of the measurement sample.

In addition, it is also possible to use image processing such as pattern matching for inputting the measurement region data. In this case, optical images of components that may be located on the measurement sample and information about whether or not the measurement is necessary are registered as measurement region data in advance. Based on this component information, the image processing is performed on the optical microscope image of the entire mapping region, and the X-ray mapping processing portion 10 automatically recognizes the measurement regions so as to perform the mapping measurement.

In addition, it is also possible to use an X-ray mapping image of the measurement sample itself as the measurement region data. In this case, the measurement regions are recognized using input information of a result of rough and short mapping measurement of the entire mapping region. Based on this information, it is determined in detail whether or not the mapping measurement is necessary in a region where a target element is detected and its vicinity, thereby performing the mapping measurement. A condition for determining whether or not the measurement is necessary can be designated for one element or for a plurality of elements. In addition, the condition may be designated for a result of a calculation process such as a logical sum or a logical multiplication of a plurality of elements multiplied by a predetermined coefficient. For instance, a region in which only Pb is detected is designated as the measurement region, or a region in which Pb and Sn are detected at a predetermined X-ray intensity ratio is designated as the non-measurement region.

Note that, the technical scope of the present invention is not limited to the embodiment described above, and various changes can be made without departing from the gist of the present invention.

For example, the description has been made of the energy dispersive fluorescent X-ray analyzer in the embodiment described above, but the present invention is also applicable to other analysis system as well, such as a wavelength dispersive fluorescent X-ray analyzer or a scanning electron microscope-energy dispersive X-ray spectrometer (SEM-EDS) capable of obtaining a secondary electron image by using an electron beam as a radiation beam to be irradiated.

In addition, the optical microscope image is used as a sample observation method in the embodiment described above, but in the present invention, other observation method, for example, a transmission X-ray image or a scanning electron microscope (SEM) image may be used.

What is claimed is:

1. An X-ray analyzer, comprising:
a sample stage on which a sample is placed;
a moving mechanism that is capable of moving the sample stage;
a radial ray source that irradiates an arbitrary irradiation point on the sample with a primary radial ray;
an X-ray detecting portion that detects a characteristic X-ray and a scattered X-ray radiated from the sample and outputs a signal including energy information of the characteristic X-ray and the scattered X-ray;
an analyzing portion that is connected to the X-ray detecting portion and analyzes the signal;
an image obtaining portion that obtains image data of the sample;
an analysis processing portion that is connected to the analyzing portion and discriminates X-ray intensity corresponding to a specific element;
an X-ray mapping processing portion that determines intensity contrast of at least one of color and brightness corresponding to the X-ray intensity based on a result of the discrimination by the analysis processing portion and performs X-ray mapping so as to perform a superimposition process of a resultant mapping image and the image data, thereby determining a position corresponding to the irradiation point;
a display portion that displays an image based on a result of the X-ray mapping; and
region designating means for designating a measurement execution region on the displayed image so as to obtain measurement region information,
wherein the moving mechanism for the sample moves at a higher speed in a region excluding the designated measurement execution region than a speed in the designated measurement execution region.

2. An X-ray analyzer according to claim 1, wherein the region designating means enables designation of the measurement execution region using drawing data of the sample stored in the X-ray mapping processing portion in advance.

3. An X-ray analyzer according to claim 1, wherein the image obtaining portion obtains one of an optically observed image and an electron microscope observation image as the sample image data in advance, and the image data is stored as reusable data.

4. An X-ray analyzer according to claim 1, wherein the X-ray mapping processing portion includes a data storing portion that stores the measurement region information about the sample that is once processed, and the measurement region information is reusable for analyzing another sample.

5. An X-ray analyzer according to claim 1, wherein the X-ray mapping processing portion uses the measurement region information with respect to image data obtained when another sample is analyzed, and performs rotational correction, positional correction, and scaling correction to precisely recognize the measurement execution region.

6. An X-ray analyzer according to claim 1, wherein the region designating means designates the measurement execution region for each cell obtained by dividing an entire mapping region into an arbitrary number of cells.

7. An X-ray analyzer according to claim 1, wherein the measurement region information comprises an X-ray mapping image obtained by roughly measuring a measurement sample itself.

* * * * *